United States Patent [19]

Antonoplos et al.

[11] 4,255,313

[45] Mar. 10, 1981

[54] NOVEL END-CAPPED POLYIMIDE OLIGOMERS

[75] Inventors: Patricia A. Antonoplos, Huntington Beach, Calif.; William J. Heilman, Houston, Tex.

[73] Assignee: Gulf Oil Corporation, Pittsburgh, Pa.

[21] Appl. No.: 31,729

[22] Filed: Apr. 20, 1979

[51] Int. Cl.[3] .............................................. C08G 73/12
[52] U.S. Cl. .................. 260/30.2; 260/30.4 N;
260/32.2; 260/31.2 N; 260/33.4 R; 260/33.2 R;
526/262; 526/259; 528/125; 526/285; 528/128;
528/170; 528/172; 528/185; 528/187; 528/226;
528/229; 528/322; 528/351; 528/352; 352/353;
560/13; 560/18; 560/36; 560/45; 560/47;
560/48; 562/427; 562/430; 562/433; 562/460;
562/466; 562/473; 562/490; 562/491; 562/492;
562/495; 525/426

[58] Field of Search ............... 526/259, 262, 263, 285;
528/125, 126, 128, 170, 172, 178, 185, 187, 226,
229, 322, 334, 351, 352, 353; 260/30.2, 30.4 N,
31.2 N, 32.2, 32.8 N, 32.2 R, 33.4 R, 326 C;
560/13, 18, 36, 45, 47, 48; 562/427, 430, 433,
460, 466, 473, 490, 491, 492, 495

[56] References Cited

U.S. PATENT DOCUMENTS

| | | | |
|---|---|---|---|
| 3,845,018 | 10/1974 | Bilow et al. | 526/285 |
| 3,864,309 | 2/1975 | Bilow et al. | 526/285 |
| 3,879,349 | 7/1975 | Bilow et al. | 526/285 |
| 3,998,786 | 12/1976 | D'Alelio | 526/285 |
| 4,058,505 | 11/1977 | D'Alelio | 526/285 |
| 4,098,767 | 7/1978 | Bilow | 526/262 |
| 4,100,138 | 7/1978 | Bilow et al. | 526/262 |

*Primary Examiner*—Lester L. Lee
*Attorney, Agent, or Firm*—Richard L. Kelly

[57] ABSTRACT

The products of the invention are end-capped polyimide oligomers prepared from a dianhydride of an aromatic tetracarboxylic acid such as 3,3'4,4'-benzophenonetetracarboxylic acid, an aromatic diamine, and a 1-(aminoaryl)-3-hydroxy-3-methyl-1-butyne. The structure of the polyimide oligomers is shown in FIG. 3.

15 Claims, 5 Drawing Figures

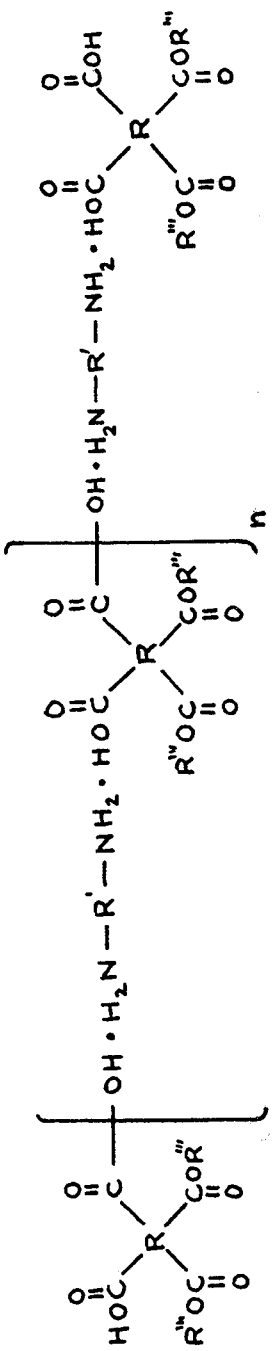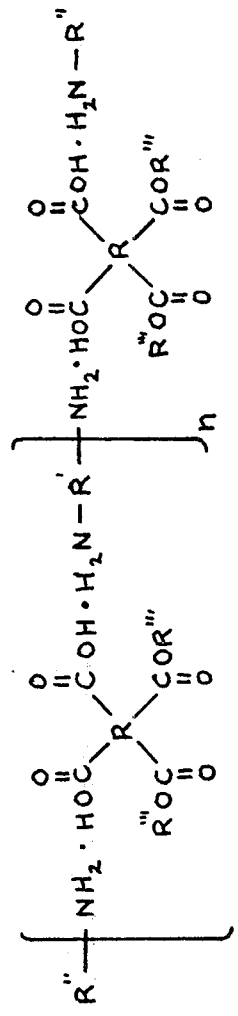
FIG. 4
FIG. 5

NOVEL END-CAPPED POLYIMIDE OLIGOMERS

BACKGROUND OF THE INVENTION

Polyimide resins prepared by the reaction of dianhydrides of aromatic tetracarboxylic acids with aromatic diamines are known products. See U.S. Pat. No. 3,179,634. Such polyimide resins are very high melting thermoplastic resins which have outstanding physical and chemical properties, including surprising stability to heat. Unfortunately, by reason of their high melting points, such resins are very difficult to fabricate by conventional techniques such as molding and extruding.

U.S. Pat. No. 3,845,018 and U.S. Pat. No. 3,897,349 disclose a somewhat related group of products prepared by reacting 1 molar portion of an aromatic diamine with 2 molar portions of a dianhydride of an aromatic tetracarboxylic acid. This product then is reacted with 2 molar portions of an acetylene substituted aromatic monoamine such as 3-aminophenylacetylene. The products are characterized as acetylene end-capped polyimide oligomers. These products can be fabricated by molding and/or laminating techniques to prepare thermoset resins having excellent heat stability. Unfortunately, the acetylene substituted aromatic monoamines are difficult to synthesize and very expensive.

There is a need in the art for polyimide resins having good physical properties, particularly heat stability, which can be readily fabricated by molding and laminating techniques, and which can be prepared at reasonable cost.

SUMMARY OF THE INVENTION

The applicants have discovered certain endcapped polyimide oligomers of excellent properties that can be prepared at modest cost, which oligomers have excellent properties as a coating and/or laminate. These products are low molecular weight polyimide oligomers in which the end-capping groups are derived from a 1-(aminoaryl) -3-hydroxy-3-methyl-1-butyne and have the structure shown in FIG. 3. The invention also is directed to two (2) precursors of the end-capped polyimide oligomers. The first precursor has the structure shown in FIG. 2. The second precursor has the structure shown in FIG. 5.

THE DRAWINGS

FIG. 4 is the chemical structure of an intermediate compound employed to prepare the compound of FIG. 5.

FIG. 5 is the chemical structure of a second precursor of the end-capped polyimides of FIG. 3.

DETAILED DESCRIPTION OF THE INVENTION

The end-capped polyimide oligomers can be prepared by two alternate synthesis methods subsequently designated as Synthesis Method A and Synthesis Method B.

Synthesis Method A

In the first step of this method, substantially two (2) mols of a dianhydride of an aromatic tetracarboxylic acid such as 3,3′,4,4′-benzophenonetetracarboxylic acid dianhydride (BTDA) are reached with one (1) mol of an aromatic diamine in a selected class of solvents under controlled temperature conditions. Letting the structure of the dianhydride be represented as

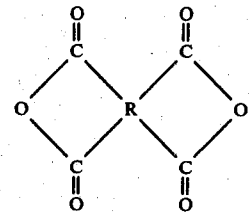

and the structure of the diamine be represented as

Figure 1:
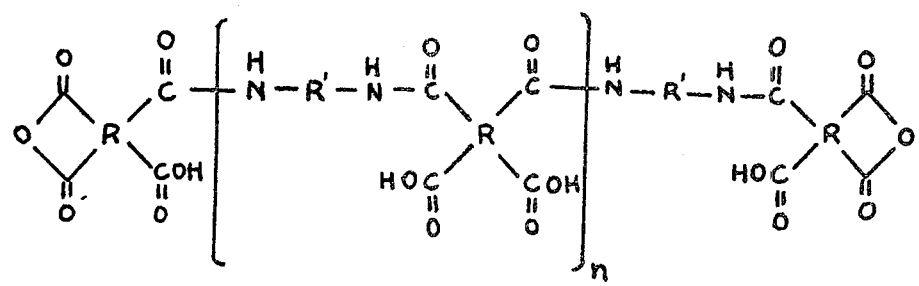
FIG. 1 is the chemical structure of an intermediate compound employed to prepare the compound of FIG. 2.

(the structure of R and R′ being defined infra) the principal product of this first reaction has the structure shown in FIG. 1.

In the second step of this method, substantially two (2) mols of a 1-(aminoaryl)-3-hydroxy-3-methyl-1-butyne are reacted with the reaction product of the first step of the process. The principal product of the second reaction has the structure shown in FIG. 2.

Figure 3:
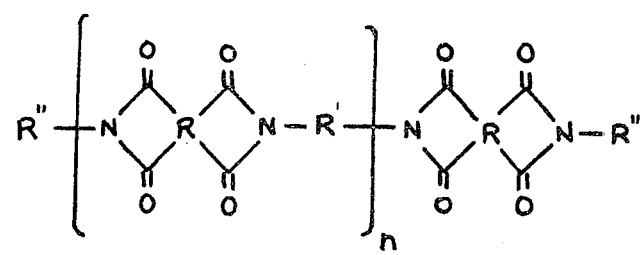
FIG. 3 is the structure of the end-capped polyimides of the invention.

In the third step of this method, the reaction product of the second step is subjected to a dehydration reaction of the type known and reported in the literature to effect ring closure of the amic-acid groups of form imide groups. The principal product of this reaction is the desired end-capped polyimide oligomer and has the structure shown in FIG. 3.

In the first step of the process, the dianhydride of the aromatic tetracarboxylic acid employed will have the structure of formula 1:

(1)

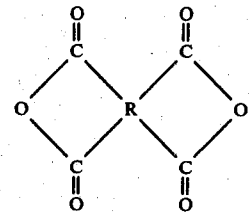

where R has the structure:

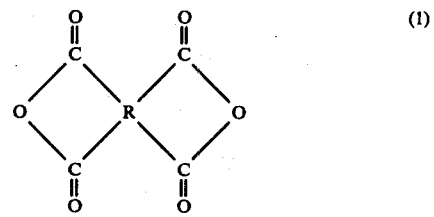

where X is

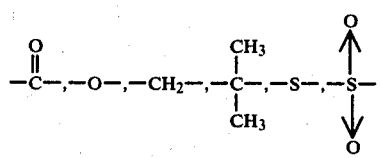

—CF$_2$—, or a bond. Examples of suitable compounds conforming to formula 1 include 3,3'4,4'-benzophenonetetracarboxylic acid dianhydride (BTDA), 3,3',4,4'diphenyl tetracarboxylic acid dianhydride, 2,2-bis(3,4-dicarboxyphenyl) propane dianhydride, bis(3,4-dicarboxyphenyl) ether dianhydride, naphthalene-1,4,5,8-tetracarboxylic acid dianhydride, bis (3,4-dicarboxyphenyl) methane dianhydride, bis(3,4-dicarboxyphenyl) sulfone dianhydride, and the like. Such compounds are known and reported in the art.

The solvent employed should be one having good solvent power for the dianhydride of formula 1 and the first intermediate product shown in FIG. 1. Suitable solvents include N-methyl-2-pyrrolidone (NMP), cyclohexanone, diethyl carbonate and gamma-butyrolactone. NMP is the solvent of choice.

In the first step of the process, the dianhydride of formula (1) such as BTDA* is heated in one of the limited class of solvents previously described, preferably NMP, to prepare a solution containing a minimum of at least 17 weight % of BTDA. In this step of the process, the BTDA should be dissolved in the solvent at a temperature substantially higher than will be employed in subsequent steps of the process. Typically the BTDA will be dissolved in the solvent at a temperature of at least 150° C. and temperatures as high as 200° C. can be employed. By operating at these temperatures, it is possible to dissolve substantially more BTDA than will dissolve at the reaction temperatures employed in subsequent steps of the process. Upon cooling such solutions to the lower temperatures subsequently employed in the reactions, it is observed that the BTDA does not precipitate but stays in solution, presumably by reason of super cooling. *Throughout the balance of the specification, BTDA will be the dianhydride referred to, but it will be understood that other dianhydrides of formula (1) also can be employed.

The quantity of BTDA dissolved in the solvent will be dictated by the solids desired in the intermediate solution and also by the quantity of solvent (if any) employed to dissolve the reactants employed in subsequent steps of the process. It is possible to prepare NMP solutions containing up to 50 weight % BTDA which remain liquid at a temperature of 50° C. It is preferred to prepare a solution containing a minimum of 17 weight % BTDA.

In the second step of the process, the hot solution of BTDA is cooled to the temperature which will be employed in the subsequent steps of the process. This temperature will be influenced by a multitude of factors. Temperatures as low as about 25° C. are sufficiently high to run the subsequent reactions, but somewhat higher temperatures may be required to maintain a sufficient quantity of BTDA in solution. Solutions of BTDA are quite viscous and increasing the temperature provides easier mixing of the reactants. Temperatures above 100° C. should be avoided, as the use of high temperatures promotes imidization of the amic acid groups present in the structure shown in FIG. 1. Such imidization is undersirable as the imide group containing products have reduced solubility in the solvent and tend to precipitate from solution. A preferred temperature range for this step of the process is about 30°–100° C. and more especially about 45°–75° C.

After the BTDA solution has been adjusted to the appropriate temperature, the aromatic diamine is added in small increments to the BTDA solution with stirring. The aromatic diamine will be added in a quantity corresponding to 0.5 molar portion per molar portion of BTDA. This reaction proceeds readily at the prevailing temperature and provides an intermediate product consisting almost exclusively of a chemical having the structure set forth in FIG. 1.

While the aromatic diamine can be added to the reaction in neat form, for convenience it normally will be dissolved in the solvent employed to dissolve the BTDA. Good stirring should be provided so that localized high concentrations of the aromatic diamine are avoided. The reaction between BTDA and aromatic diamine is exothermic and cooling should be provided to maintain the temperature within the limits previously discussed.

In the structure shown in FIG. 1, n will have a value of 0 and 2 moles of BTDA have reacted with 1 mol of the aromatic diamine. This ordinarily is the preferred species and is obtained when the previously described 2/1 molar ratio is employed and the aromatic diamine is added to the BTDA in small increments with good stirring. Some small quantity of the aromatic diamine will react with the previously formed preferred species to form low polymers such as dimers, trimers, etc., where n has a value such as 1, 2, 3, or the like. In most products, n will have an average value such as 0.1, 0.2, etc. In cases where it is desired to increase the molecular weight somewhat, the ratio of aromatic diamine to BTDA can be increased from an 0.5/1.0 ratio up to about 0.8/1.0.

The aromatic diamine employed has the structure $$H_2N—R'—NH_2 \qquad (2)$$

where R' is a phenylene group, a naphthylene group, or

, or
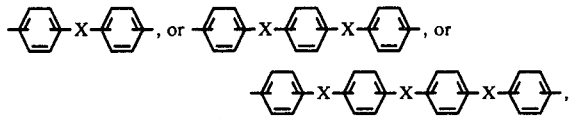

and where X has the same meaning as in formula (1) supra. Examples of suitable aromatic diamines include 4,4'-diamino-diphenyl sulfide, 3,3'diamino-diphenyl sulfone, 3,3'dimethyl-4,4'diaminodiphenylmethane, 3,3'dimethyl-4,4'diaminodiphenylether, meta and paraphenylene diamine, 1, 7-naphthyl diamine, 4,4'-methylene dianiline and 4,4'-oxydianiline. The presently preferred aromatic diamines are the bis (aminophenoxy) benzenes (APB), and preferably 1, 3-bis (3-aminophenoxy) benzene. Such compounds are known and reported in the art. The bis-aminoaryl methanes, such as 4,4-methylene dianiline, customarily are prepared by condensing aniline (or equivalent) with formaldehyde. In this synthesis small precentages of a coproduct are prepared by condensing another mol of aniline and formaldehyde with the desired 4,4-methylene dianiline, viz., 2,4-bis-(p-aminobenzyl) aniline (BPABA). No purification is required so long as the BPABA is not present in a concentration greater than about 0.3 mol per mol of 4,4-methylene dianiline.

Figure 2:
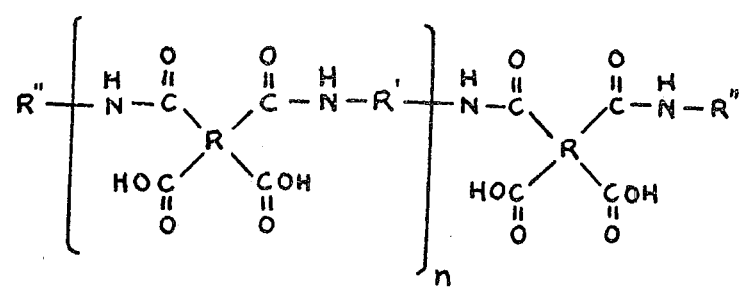
FIG. 2 is the chemical structure of a precursor of the end-capped polyimides of FIG. 3.

In the next step of the process, a 1-(aminoaryl)-3-hydroxy-3-methyl-1-butyne (AHMB) is added to the reaction product of the previous step. The addition is made in small increments with stirring to the solvent solution of the intermediate product prepared in the previous step of the process. The compound can be added in neat form, or as a concentrated solution in the solvent employed in the earlier steps of the process. Good stirring and cooling should be provided to maintain a reaction temperature within the limits previously described. The AHMB is added in a molar quantity equivalent to the molar quantity of BTDA charged to the first step of the process. The reaction product is a solution of a chemical having the structure shown in FIG. 2. In the formula of FIG. 2, n has a minimum value of at least 1 and can have an average value of as high as 4 when the ratio of the aromatic diamine to BTDA is increased to about 0.8/1.0 in the previous step of the process.

The 1-(aminoaryl)-3-hydroxy-3-methyl-1-butynes employed have the structure:

$$H_2N-R'' \qquad (3)$$

where R'' has the structure:

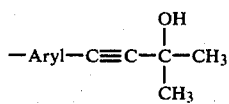

where Aryl has the same structure as R' in formula (2). Examples of suitable members of the class include the 1-(aminophenyl)-3-hydroxyl-3-methyl-1-butynes (AHMB), which can consist of various position isomers depending upon the position occupied by the amino group on the phenyl ring, and corresponding analogues in which the aminophenyl group is replaced with other aminoaryl groups such as the isomeric aminotolyl groups, the isomeric aminoxylyl groups, the isomeric aminonaphthyl groups and the like.

The 1-(aminoaryl)-3-hydroxy-3-methyl-1-butynes employed in the present invention are known compounds described in U.S. Pat. No. 4,139,561 issued to Onopchenko et al. These compounds can be prepared from the corresponding nitroaromatic analogues by selective hydrogenation of the nitro group in the presence of a ruthenium catalyst. The nitroaromatic analogues can be prepared by reacting a corresponding nitroaryl acetylene with a ketone in the presence of sodium hydroxide in liquid ammonia.

The product of the preceding step can be converted to the desired end-capped polyimide oligomer by effecting ring closure of the amic acid groups by a dehydration reaction. Such methods are reported in the art, particularly the Barie patent U.S. Pat. No. 4,097,456 whose descriptions are incorporated herein by reference.

Synthesis Method B

In the first step of this method substantially two (2) mols of certain diesters of an aromatic tetracarboxylic acid such as a dialkyl ester of 3,3',4,4' benzophenonetetracarboxylic acid are reacted with one (1) mol of an aromatic diamine of formula (2) in a suitable solvent to form an amine salt. Letting the dialkyl ester of the aromatic tetracarboxylic acid be represented as:

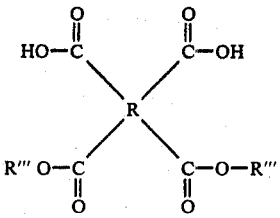

(the structure of R and R''' being defined infra), the principal product of this first reaction has the structure shown in FIG. 4, with n having the same value as in the formula of FIG. 1.

In the second step of this method, 1-(aminoaryl)-3-hydroxy-3-methyl-1-butyne, preferably AHMB, is reacted with the reaction product of the first step of the process to form a complex amine salt having the structure shown in FIG. 5, with n having the same value as in FIG. 2.

In the third step of this method, the reaction product of the second step is heated to effect a ring closure to form imide groups. The product of this step is the desired end-capped polyamide oligomer.

The dialkyl esters of the aromatic tetracarboxylic acid employed in the first step of the process have the formula:

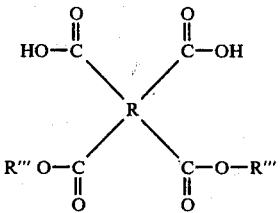

where R has the same meaning as in formula (1) and where R''' is the moiety derived from a suitable alcohol, preferably an alkanol containing up to about 5 carbon atoms. It will be recognized that 3 position isomers are possible for each diester, all of which are functional equivalents in the present invention. The desired dialkyl esters can be prepared by reacting 1 molar portion of a dianhydride of formula (1), e.g., BTDA, with 2-molar portions of a lower alkanol containing up to 5 carbon atoms. An excess of the alkanol can be used as the reaction solvent and only the desired dialkyl ester will be formed under proper reaction conditions.

In the first step of the process, the diester of the aromatic tetracarboxylic acid, e.g., a diester of BTDA, is reacted with the aromatic diamine in a suitable solvent. Typically, the solvent employed will be the alkanol from which the diester is prepared. If desired, however, other lower alkanols containing up to about 5 carbon atoms can be employed, preferably such solvents having atmospheric boiling points of less than 150° C. If desired, mixtures of solvents can be employed including mixtures of an alcohol or an ether with water. Each of the chemicals is dissolved in the minimum required quantity of the solvent.

This first reaction preferably is run by adding the aromatic diamine solution in small increments to the solution of the diester. Good stirring is provided so that localized high concentrations of aromatic diamine are avoided for reasons essentially similar to those noted respecting the first step of Synthesis Method A previously discussed.

The value of n in this product can be increased by increasing the molar ratio of diamine to diester from about 0.5/1.0 up to about 0.8/1.0 to form dimers, trimers, and the like. The controlling factors are as previously described with respect to Synthesis Method A.

In the next step of the process, a 1-(aminoaryl)-3-hydroxy-3-methyl-1-butyne of formula (3), such as AHMB, is added in small increments with stirring to the solvent solution of the intermediate product produced in the previous step of the process. The majority of these compounds are liquids at ambient temperature and can be added to the reaction in neat form, or as a concentrated solution in the same solvent employed in the earlier steps of the process.

In the final step of this method, the reaction product of the second step is heated to effect a ring closure to form imide groups. This step preferably is carried out employing the techniques disclosed in the pending Antonoplos et al application Ser. No. 956,708, filed Nov. 1, 1978, which disclosure is incorporated herein by reference. The Antonoplos et al application is owned by the assignee of the present application.

Utility of Products

The end-capped polyimide oligomers can be used to lay down tough coatings on substrates such as metals and to prepare laminates and/or composite structures. To prepare such structures, a web or inorganic fibers such as glass, quartz, graphite fibers or the like, is impregnated with a solution containing the polyimide solids. The impregnated web then is heated to cross-link the oligomer. The coatings and laminates have excellent strength, which strength is retained to a surprising degree even after the articles are heated for extended periods oof time at elevated temperatures, e.g., 500 or more hours at 315° C. (600° F.). Moreover, the products, before being cured, have excellent flow so that laminates and composites prepared therefrom are uniform throughout and free of voids.

It also is possible and frequently desirable to prepare such compositions from one of the precursors of the polyimide oligomer. Either of the two previously described precursors, i.e., of the structure shown in FIG. 2 or FIG. 5, can be employed. When the precursors are heated, they form the polyimide structure shown in FIG. 3 and upon further heating form cross-linked products. The advantage of employing the precursors is that they have a much higher solubility in solvents. As a consequence, higher solids levels can be incorporated into the laminate or composite. It is possible to prepare solution which contain at least 30 weight% of the product of FIG. 2 in solvents such as NMP. It is possible to prepare solutions containing at least 50 weight% of the product of FIG. 5 in solvents such as the 1–5 carbon alkanols.

Where desired, the intermediates of FIG. 5 can be converted to a solid state for storage or shipment by careful spray durig employing the conditions set forth in the Antonoplos et al application Ser. No. 956,708, filed Nov. 1, 1978, and earlier incorporated herein by reference. These solids then can be dissolved in a suitable solvent of the type previously described to prepare coating and/or laminating solutions.

When used as coating compositions, the precursor solution should be laid down on the substrate and heat cured at temperatures of 175° C. or higher. To prepare laminates, the desired web should be impregnated with a precursor solution and heated to an elevated temperature for a time sufficient to convert the precursor solids to imides and liberate water. Drying the impregnated web for 60 minutes to 150° C. or 80 minutes at 135° C. in a circulating air oven is usually sufficient. The dried webs then can be laid up and heated under pressure to cross-link the resin solids. Modest pressures of the order of 15–200 psig are sufficient. Curing temperatures of the order of 177°–260° C. and preferably 195°–220° C. are employed for curing times of the order of 1–12 hours. Optimum properties are developed by post curing the laminates for periods of 16–48 hours at temperatures of about 260°–375° C.

It has been observed that up to 50 mol % of the 1-(aminoaryl)-3-hydroxy-3-methyl-1-butyne employed in preparing the products of the invention can be replaced with an unsubstituted aromatic monoamine such as aniline, the alkyl substituted anilines such as isomeric toluidines and xylidenes, the naphthyl amines, the monoamino substituted biphenyls and the like. Aniline is preferred for this purpose.

The following examples are set forth to illustrate the principle and practice of the invention to those skilled in the art. Where parts and percentages are set forth, unless otherwise noted, they are parts and percentages expressed on a weight basis.

EXAMPLE 1

Part A

Charge 40 ml of NMP and 32.2 grams (0.10 mol) of BTDA to a reaction vessel equipped with a high-powered stirrer. Heat the mixture to 150° C. with stirring to dissolve all the BTDA and then cool to 60° C. Add a solution of 14.6 grams (0.05 mol) of 1,3-bis-(3-aminophenoxy) benzene (APB) dissolved in 20 ml of NMP dropwise over a period of 1 hour. Cool the vessel to maintain the reaction temperature at about 60° C. The product will have the structure shown in FIG. 1.

Part B

Add 17.5 grams (0.10 mol) of 1-(3-aminophenyl)-3-hydroxy-3-methyl-1-butyne (AHMB) dropwise with stirring over a period of 1 hour to the solution of Part A while cooling the vessel to maintain a reaction temperature of about 60° C. The product will have the structure shown in FIG. 2. The NMR spectrum of the product will show no detectable concentration of imide groups.

Part C

Charge the product of Part B and 300 ml of toluene to a flask equipped with a Dean-Stark Trap. Heat to reflux to effect a ring closure to form imide groups and remove the liberated water as an azeotrope. In about 4 hours the theoretical quantity of water is collected. Recover the product by pouring it into about 2 liters of ethanol to precipitate a product consisting principally of a compound having the structure shown in FIG. 3. The yield is essentially quantitative.

EXAMPLE 2

Part A

Charge 30 grams (0.66 mol) of ethanol and 32.2 grams (0.10 mol) of BTDA to a reaction vessel equipped with a high-powered stirrer. Heat the mixture to reflux with stirring until all of the BTDA is esterified to form the diethyl ester of BTDA. The solution, when cooled to ambient temperature, has a viscosity of about 2,500 cps at 25° C. Add a solution of 14.6 grams (0.05 mol) of APB dissolved in 80 grams of ethanol dropwise with stirring over a period of about 15 minutes. The solution this prepared will contain about 35 weight % solids. Distill approximately 80 grams of ethanol to prepare a solution containing about 75 weight % solids. The product will consist principally of an amine salt having the structure shown in FIG. 4.

Part B

Add a total of 17.5 grams (0.10 mol) of AHMP dropwide with stirring over a period of 15 minutes to the product A. The product contains about 78 weight % solids and has a viscosity of about 75,000 cps at 25° C. The product will consist principally of an amine salt having the structure shown in FIG. 5.

Part C

Inject the product of Part B onto the rotating flask of a rotary evaporator heated to about 90° C. and operated at about 1 mm of Hg. This product is partially imidized. Heat this product for 20 ;1 minutes at 130° C. in a vacuum oven operated at 1 mm of Hg. to complete the imidization reaction. The product is essentially identical to the product of Example 1, Part C.

EXAMPLE 3

Impregnate six-inch squares of 181 E glass cloth (with an A-1100 finish) with the resin solution of Example 1, Part B. Dry these samples for 30 minutes in a circulating air oven at 150° C. Extract a specimen of the dried fabric with NMP for chromatographic, NMR and I.R. analysis. The extracted product will contain no evidence of carboxyl groups, thus indicating that all of the amic acid groups have been converted to imide groups.

EXAMPLE 4

Lay up six pieces of 181 E glass fabric from Examples 3 in the form of a laminate, place in a press under a pressure of 200 psig, and heat for two hours at 250° C. The laminate will be medium brown in color and contain approximately 25 weight % resin. Postcure the laminate for four hours at 650° F. (343° C.) and then an additional 15 hours at 700° F. (370° C.). No blisters or voids will be present in the postcured laminate.

EXAMPLE 5

Impregnate six-inch squares of 181 E glass cloth fabric (with an A-1100 finish) with the resin solution of Example 2, Part B. Dry these samples overnight at room temperature and then heat for 30 minutes in a circulating air oven at 190° C. The dried fabric will contain about 35 weight % resin solids.

When an attempt is made to extract resin solids from the dried glass fabric with ethanol, only a small percentage of the solids is extracted. This fact suggests that the resin solids have undergone a chemical reaction during the drying step. When the dried glass fabric is extracted with N-methyl-2-pyrrolidone (NMP), an extract is recovered which is soluble to the extent of about 3 weight % in the NMP at room temperature. No detectable quantity of carboxylic acid protons will be present in the spectrum. The IR spectrum of the NMP extract is essentially identical to the product of Example 1, Part C.

EXAMPLE 6

Part A

Graphite tapes 5" wide are impregnated with the resin solution prepared in Example 2, Part B. The fibers are a commercial product sold under the name Celion 3000, have an 0 twist, and bear an NR 150-B2 surface size. The impregnated tapes are dried until the tapes contain 40 weight % resin solids. The prepregs are 2.5 mls thick. A laminate lay up is made from 32 plys with the prepegs all being aligned in one direction. The lay up is laminated by a vacuum bag technique with the assembly being heated from ambient temperature to 260° F. with the temperature being increased at a rate of 5°/minute under a vacuum of 15 inches of Hg. The assembly is maintained for an additional 2-hour period under 15 inches of Hg. The pressure then is reduced to the maximum vacuum that can be drawn and the temperature is increased to 485° F. at a rate of about 7° F./minute. The laminate is held at 485° F. for an additional period of 2 hours. The laminate is cooled to room temperature over a period of 5 hours. The laminate is post cured by heating from room temperature to 650° F. at a rate of 5 -10° F./minute and then heating for 13 hours at 650° F. The temperature then is increased to 700° F. at a rate of 5°-10° F./minute. The temperature then is held at 700° F. for an additional 4 hours.

The short Beam Shear, Flexural Strength, and Tangent Modulus of Elasticity, as determined by ASTM procedures at room temperature and at 600° F., are substantially as set forth in Table I.

TABLE I

| Property | Room temperature Value | 600° F. Valve |
| --- | --- | --- |
| Short Beam Shear | 12 ksi | 7 ksi |
| Flexural Strength | 200 ksi | 140 ksi |
| Tangent Modulus of Elasticity | 20,000,000 ksi | 19,000,000 ksi |

Part B

Specimens of the laminates prepared in Part A, when heated for 300 hours at 600° F., show a weight loss of only about 2%.

What is claimed:

1. A product selected from the group consisting of:
  A. An acetylene end-capped polyimide oligomer having the structure:

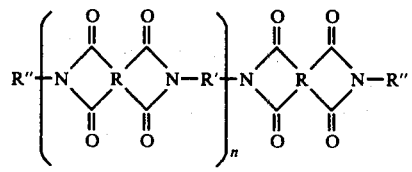

where R has the structure:

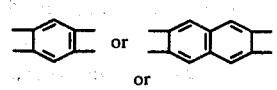

or

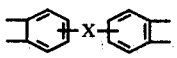

$$-\overset{O}{\underset{\|}{C}}-,\ -O-,\ -CH_2-,\ -S-,\ -\overset{\overset{O}{\uparrow}}{\underset{\underset{O}{\downarrow}}{S}}-,\ -\overset{CH_3}{\underset{CH_3}{\overset{|}{\underset{|}{C}}}}-,$$

where X is
—$CF_2$—, or a bond, where R' is selected from the group consisting of a phenylene group, a naphthylene group, or

[structures], or [structures], or

[structure], where X is as defined above; and
where R" is an aryl group bearing a substituent having the structure:

$$-C\equiv C-\overset{OH}{\underset{CH_3}{\overset{|}{\underset{|}{C}}}}-CH_3;$$

B. A first precursor of an acetylene end-capped polyimide oligomer of (A) having the structure:

[structure]

where R, R' and R" are as defined above; and

C. A second precursor of an acetylene end-capped polyimide oligomer of (A) having the structure:

[structure]

where R, R' and R" are as defined above and R'" is the alcohol moiety from which the diester of the aromatic tetracarboxylic acid was prepared where in each of the above formulas n has an average value from 1 to about 4.

2. An acetylene end-capped polyimide oligomer having the structure:

[structure]

where R has the structure:

[structures] or [structures]

or

[structure]

$$-\overset{O}{\underset{\|}{C}}-,\ -O-,\ -CH_2-,\ -S-,\ -\overset{\overset{O}{\uparrow}}{\underset{\underset{O}{\downarrow}}{S}}-,\ -\overset{CH_3}{\underset{CH_3}{\overset{|}{\underset{|}{C}}}}-,$$

where X is
—$CF_2$—, or a bond, where R' is selected from the group consisting of a phenylene group, a naphthylene group, or

[structure], or

[structure], or

[structure]

where X is as defined above; and where R" is an aryl group bearing a substituent having the structure:

$$-C\equiv C-\overset{OH}{\underset{CH_3}{\overset{|}{\underset{|}{C}}}}-CH_3$$

and where n has a value of from 1 to about 4.

3. A precursor of an acetylene end-capped polyimide oligomer having the structure:

[structure]

where R has the structure:

[structures] or [structures]

or

-continued

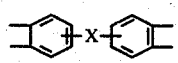

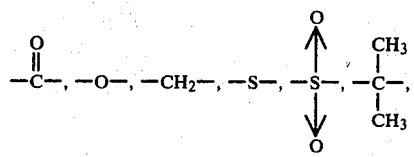

where X is
—CF$_2$—or a bond; where R' is selected from the group consisting of a phenylene group, a naphthylene group, or

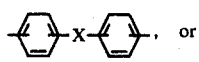

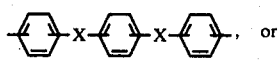

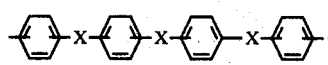

where X is as defined above; and where R" is an aryl group bearing a substituent having the structure:

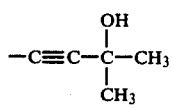

and where n has a value of from 1 to about 4.

4. A precursor of an acetylene end-capped polyimide oligomer having the structure:

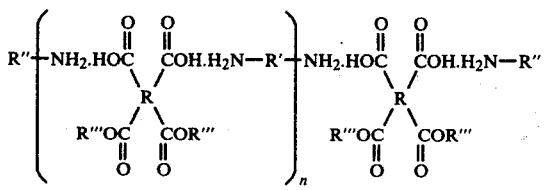

where R has the structure:

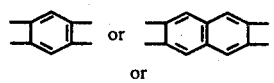

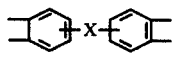

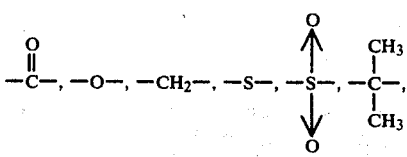

where X is

—CF$_2$—or a bond; where R' is selected from the group consisting of a phenylene group, a naphthylene group, or

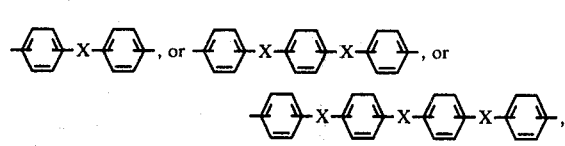

where X is as defined above; where R" is an aryl group bearing a substituent having the structure:

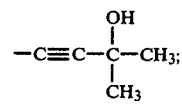

and where R'" is the alcohol moiety from which the diester of the aromatic tetracarboxylic acid was prepared and where n has a value of from 1 to about 4.

5. A product of claim 1, 2, 3, 4 in which R has the structure:

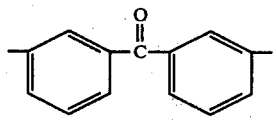

and where R" has the structure:

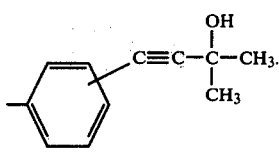

6. A coating and laminating varnish consisting essentially of a product of claim 3 dissolved in a solvent selected from the group consisting of N-methyl-2-pyrrolidone, cyclohexanone, diethyl carbonate, and gamma-butyrolactone.

7. A coating and laminating varnish consisting essentially of a product of claim 4 dissolved in a solvent having an atmospheric boiling point of less than about 150° C. and selected from the group consisting of lower alkanols containing up to about 5 carbon atoms, lower ethers containing up to about 6 carbon atoms, and mixtures thereof.

8. A product of claim 1, 2, 3, 4, 6 or 7 in which up to 50 mol % of the terminal

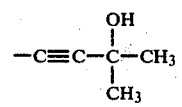

groups of R" is replaced with a hydrogen atom.

9. A process for preparing a product of claim 4 which consists essentially of:
   a. Dissolving at least 17 weight % of an aromatic tetracarboxylic acid dianhydride in a solvent at a temperature of at least 60° C.,
   b. Maintaining a solution of step (a) containing substantially 1 molar portion of said aromatic tetracarboxylic acid dianhydride at a temperature in a range of about 30°–100° C. and adding substantially 0.50 molar portion of an aromatic diamine thereto and forming a reaction product consisting essentially of a chemical having the structure:

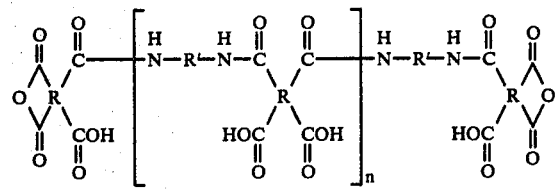

c. Adding substantially 1.0 molar portion of an aromatic monoamine to the product of step (b) and forming a reaction product consisting essentially of a chemical having the structure:

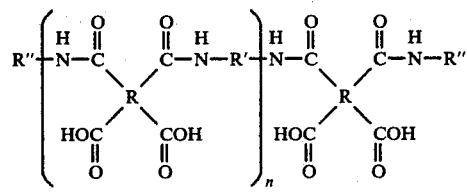

said aromatic tetracarboxylic acid dianhydride having the formula:

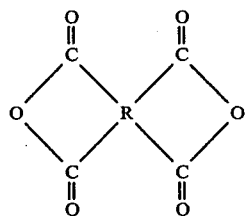

where R has the structure:

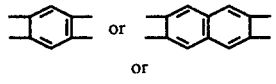

or

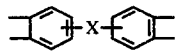

where X is

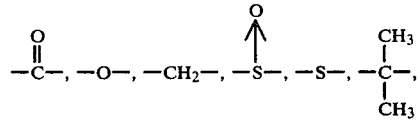

—CF$_2$—, or a bond; said aromatic diamine having the formula:

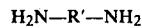

H$_2$N—R'—NH$_2$ where R$^1$ is selected from the group consisting of a phenylene group, a naphthylene group, or

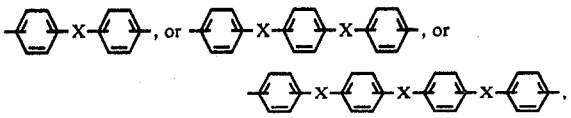

where X is as defined above; and said aromatic monoamine having the formula:

R"—NH$_2$;

where R" is an aryl group bearing a substituent having the structure:

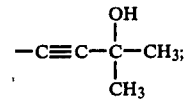

and the solvent employed in step (a) is selected from the group consisting of N-methyl-2-pyrrolidone, cyclohexanone, diethyl carbonate, and gamma-butyrolactone where in each of the above formulas n has an average value from 1 to about 4.

10. A process for preparing a product of claim 4 which consists essentially of:

A. Adding, with stirring a solution containing substantially 0.50 molar portion of an aromatic diamine to a solution containing substantially 1.0 molar portion of a dialkyl ester of an aromatic tetracarboxylic acid, and B. Adding substantially 1.0 molar portion of an aromatic monoamine to the solution of (A);

said dialkyl ester of the aromatic tetracarboxylic acid having the formula:

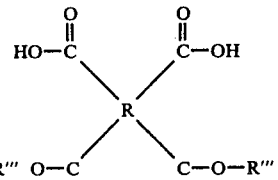

where R has the structure:

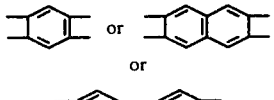

or

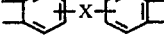

where X is

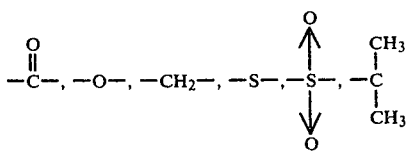

—CF$_2$—, or a bond, and where R''' is the moiety of an alkanol containing up to about 5 carbon atoms; said aromatic diamine having the formula:

$H_2N-R'-NH_2$ where R' is selected from the group consisting of a phenylene group, a naphthylene group, or

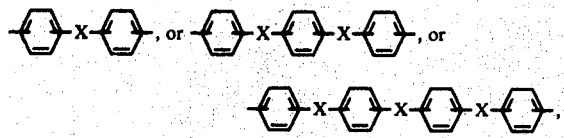

where X is as defined above; and said aromatic monoamine having the formula:

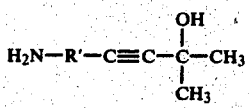

where R' is an aryl group; and the solvent employed in step (A) having an atmospheric boiling point of less than about 150° C. and is selected from the group consisting of lower alkanols containing up to about 5 carbon atoms, lower ethers containing up to about 6 carbon atoms, and mixtures thereof.

11. A process of claim 9 or 10 in which R has the structure:

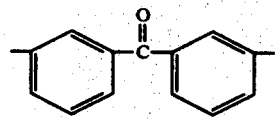

and where R" has the structure:

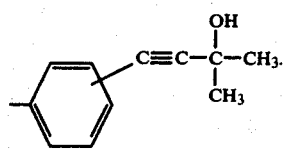

12. A process for preparing a product of claim 2 which consists essentially of preparing a product of claim 3 by the method of claim 9 and effecting ring closure of the amic acid groups by a dehydration reaction.

13. A process for preparing a product of claim 2 which consists essentially of preparing a product of claim 4 by the process of claim 10 and heating said product to effect a ring closure to form imide groups.

14. A process of claim 12 or 13 in which R has the structure:

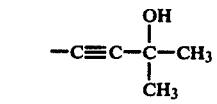

and where R" has the structure:

$$\begin{array}{c} OH \\ | \\ C\equiv C-C-CH_3. \\ | \\ CH_3 \end{array}$$

15. A process of claim 9, 10, 12, or 13 in which up to 50 mol % of the terminal $$\begin{array}{c} OH \\ | \\ -C\equiv C-C-CH_3 \\ | \\ CH_3 \end{array}$$

groups of R" is replaced with a hydrogen atom.

* * * * *